United States Patent [19]

Hoekstra et al.

[11] Patent Number: 5,254,802

[45] Date of Patent: Oct. 19, 1993

[54] MALE STERILE BRASSICA PLANTS

[76] Inventors: Sietske Hoekstra, Montferlandstraat 2<sup>II</sup>, NL 1079 PJ Amsterdam; Arnoldus J. Kool, Kerkeland 74, NL-1602 LJ Enkhuizen; Maria G. Nootebos, Gruttolaan 36, NL-1602 PJ Enkhuizen; Mei-Lie M. C. Ian, Kastanjelaan 76, NL-1602 SM Enkhuizen, all of Netherlands

[21] Appl. No.: 625,326

[22] Filed: Dec. 10, 1990

Related U.S. Application Data

[63] Continuation of Ser. No. 479,871, Feb. 14, 1990, abandoned, which is a continuation of Ser. No. 285,182, Dec. 15, 1988, abandoned.

[30] Foreign Application Priority Data

Dec. 17, 1987 [GB] United Kingdom ................. 8729403
Mar. 29, 1988 [GB] United Kingdom ................. 8807501
Sep. 1, 1988 [GB] United Kingdom ................. 8820643

[51] Int. Cl.$^5$ ........................ C12N 5/14; C12N 15/05; A01H 4/00
[52] U.S. Cl. ........................... 800/220; 800/DIG. 16; 435/240.47; 435/240.49; 435/240.51; 435/172.2; 935/91; 935/94; 935/96; 935/98
[58] Field of Search ............. 435/172.2, 240.4, 240.47, 435/240.49, 240.51; 935/90, 91, 94, 96, 98; 800/220, DIG. 15, DIG. 16, DIG. 17

[56] References Cited

FOREIGN PATENT DOCUMENTS 139674 3/1984 European Pat. Off. .
214601 9/1986 European Pat. Off. .
267753 11/1987 European Pat. Off. .
8403606 9/1984 World Int. Prop. O. .

OTHER PUBLICATIONS

Barsby et al. (1987) Theor. Appl Genet. 73: 809-814.
Barsby et al. (1987) Plant Science 53: 243-248.
Evans et al, eds. Handbook of Plant Cell Culture, vol. 1 MacMillan, 1983, pp. 376-385.
Robertson, et al. (1986) Plant Cell Reports 5: 61-64.
Carter et al. (1987) Protoplast Symposium pp. 181-182.
Zelcer et al. (1978) Z. Pflanzenphysiol Bd. 90 S.: 397-407.
Sidorov, et al. (1981) Planta 152: 341-345.
Menczel et al. (1987) Plant Cell Reports 6: 98-101.
Sundberg et al. (1986) Plant Science 43: 155-162.
Yarrow, 1990 Methods in Molecular Biology (Pollard, et al., Eds) Humana Press pp. 381-396.
Aviv, et al. 1984 Mol. Gen. Genet. 196: 244-253.
Ichikawa, et al. 1987 Theor. Appl. Genet. 74: 746-752.
Glimelius, K. 1984 "High growth rate and regeneration capacity of hypocotyl protoplasts in some Brassicaceae" Physiol. Plant. 61: 38-44.
Horne et al. "Genetic Manipulation in Plant Breeding, Proceeding of International Symposium, Sep. 8-13, 1985, West Berlin" Walter D. Gruyter and Co. 653-661.
Vedel et al. Curr. Genet. 11(1):17-24 1986.
Vedel et al. Plant Physiol. Biochem. 25(3):249-257, 1987.
Mantell et al. "The Chondriome, Chloroplast and Mite Chondriome Genomes" Longmans 192-210, 1986.
Pelletier et al. Mol. Gen. Genet. 191:244-250, 1983.
Barsby et al. Plant Molecular Biology, Diter von Wettstein and N-H Chua, Eds, Plenum Publishing Corp. 223-234, 1987.
Robertson et al. Forest and Crop Biotechnology-Progress and Perspectives (Proceeding of the Symposium on Apr. 17-19, 1985, Syracuse, N.Y.) Eds. Valentine, Springer, Verlag.
Robertson et al. Plant Cell Reports 5:61-64, 1986.
Robertson et al. Eucarpia Cruciferae Newsletter 9:39-40, 1984.
Robertson et al. 1987. "Analysis of Organelle Genomes in a Somatic Hybrid Derived from . . . " Theor. Appl. Genet. 74:303-309.
Pelletier et al. 1986. "Genetic Improvement of Cytoplasmic Traits . . . " Genetic Manipulation in Plants Breeding Proc. Intl. Symp. 1985 pp. 653-661.
Vedel et al. 1987. "Mitochondrial DNA Variation in Cytoplasmic Male Sterile Somatic Hybrids of Brassica napus" Plant Physiol. Biochem. 25(3):249-257.
Simmonds et al. 1979. Principles of Crop Improvement Longman Group, Ltd. New York pp. 224-239.

Primary Examiner—Che S. Chereskin
Attorney, Agent, or Firm—Allen E. Norris

[57] ABSTRACT

Brassica oleracea plants having cytoplasmic male sterility and processes for their production.

6 Claims, 1 Drawing Sheet

MALE STERILE BRASSICA PLANTS

This is a continuation of application Ser. No. 07/479,871, filed Feb. 14, 1990 now abandoned which in turn is a continuation division of application Ser. No. 07/285,182, filed Dec. 15, 1988, now abandoned.

This invention concerns the development of new parental lines of *Brassica oleracea*. The parental lines are used to produce hybrid seed. Specifically this invention enables a plant breeder to incorporate the desirable quality of cytoplasmic male sterility (CMS) into a commercially desirable variety of *B oleracea*.

Male sterility is of value in *B oleracea* hybrid seed breeding because normal flowers are self-pollinating. Male sterile lines do not produce viable pollen and cannot self-pollinate. By eliminating the pollen of one parental variety in a cross, a plant breeder is assured of obtaining hybrid seed of uniform quality. At present cytoplasmic male sterility is not readily available in *B oleracea* varieties. Commercial producers of hybrid seed use nuclear self-incompatibility systems to avoid self-pollination during seed production. This system is inaccurate and results in impure hybrid seed lots. Also, it is time consuming, laborious and thus costly to introduce this genetic system into all breeding lines. In *Raphanus sativus* a cytoplasm has been discovered that confers male sterility. This cytoplasm is known as Ogura CMS cytoplasm and the DNA from the mitochondria and chloroplasts contained in the cytoplasm is genotypically different from the DNA in the cytoplasm of fertile *B oleracea* plants. The Ogura type CMS cytoplasm can be introduced in *B oleracea* by repeated back crosses. In the resulting Ogura CMS *B oleracea* plants the mitochondria of *R sativus* result in a CMS phenotype. The presence of the chloroplasts of *R sativus* however results in chlorosis when the plants are grown at low temperature which consequently results in yield losses. This makes this type of Ogura CMS *B oleracea* plant of little use in commercial hybrid seed production.

The present invention provides *B oleracea* plants having mitochondria of the Ogura CMS cytoplasm and cold tolerant chloroplasts of normal fertile *B oleracea*. The plants according to the invention have cytoplasmic male sterility, but will not show chlorosis when grown at low temperature.

The present invention further provides a process of preparing *B oleracea* plant material having cytoplasmic male sterility and commercially desirable nuclear traits, which do not show chlorosis when grown at low temperatures. Such CMS *B oleracea* plants are obtained by fusion of *B oleracea* protoplasts having commercially desirable nuclear traits with inactivated or nucleus-free protoplasts of an Ogura CMS *B oleracea* plant, followed by regeneration into plants of the thus obtained allogenic cells.

The present invention is particularly suitable for the production of CMS in the following *B oleracea* varieties:

1 *Brassica oleracea L. convar. acephala* (DC.) *Alef. var. botrytis L.* (cauliflover)

2 *Brassica oleracea L. convar. capitata* (L.) *Alef. var. alba DC* (white cabbage)

3 *Brassica oleracea L. convar. oleracea var. gemmifera DC* (Brussels sprouts)

4 *Brassica oleracea L. convar. acephala* (DC.) *Alef. var. sabellica L.* (curly kale)

5 *Brassica oleracea L. convar. capitata* (L.) *Alef. var. sabauda L.* (Savoy cabbage)

6 *Brassica oleracea L. convar. capitata* (L.) *Alef. var. rubra DC.* (red cabbage)

7 *Brassica oleracea L. convar. acephala* (DC.) *Alef. var. gongylodes* (Kohlrabi)

8 *Brassica oleracea L. convar. botrytis* (L.) *Alef. var. cymosa Duch* (broccoli)

and more preferably in cauliflower, white cabbage, Brussels sprouts and broccoli as identified above.

Figure 1:
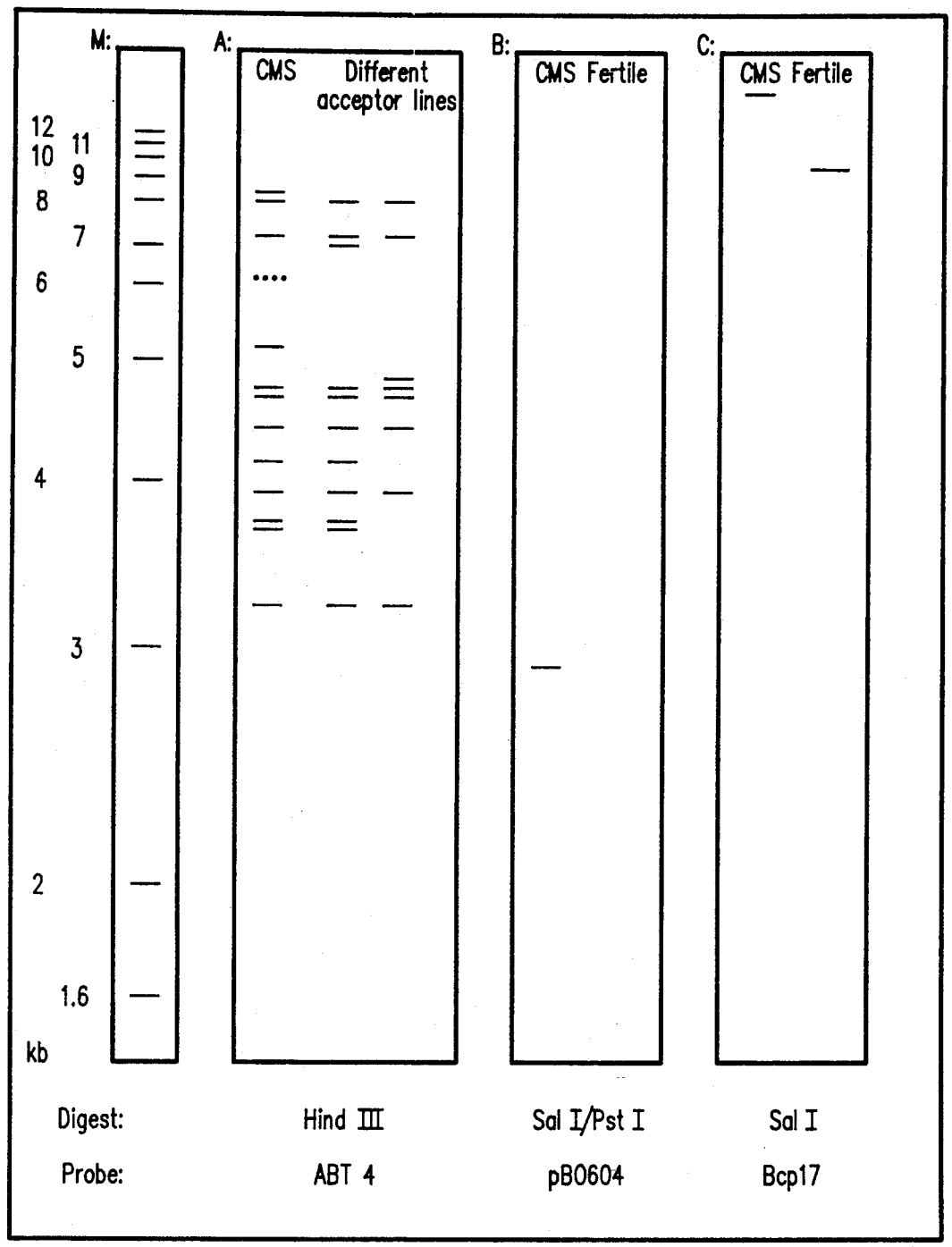
FIG. 1 is a drawing of a photograph of the results of endonuclease digest. Panel M shows molecular weight standards. Panel A shows hybridisation pattern of CMS donor *B. oleracea* A61043 and various acceptor lines with ABT 4. Panel B shows hybridisation of mitochondrial DNA from Ogura CMS cytoplasm of *B. oleracea* A61043 (left) and mitochondrial DNA of *B. oleracea* breeding lines (right) with pB0604. Panel C shows hybridisation of Ogura CMS chloroplast DNA (left) and fertile cytoplasms of *B. oleracea* breeding lines (right) with Bcp17.

The term Ogura CMS cytoplasm as used herein refers to *Raphanus sativus* originating cytoplasm comprising mitochondrial DNA which confers male sterility to plants. The term Ogura CMS *Brassica oleracea* plant or plant cell as used herein refers to a *Brassica oleracea* plant or plant cell comprising Ogura CMS cytoplasm.

The protoplast fusion according to the invention may be accomplished by employing polyethylene glycol (PEG) causing agglutination, in the presence of a fusion buffer, i.e. a high pH solution to let the membranes fuse. Such somatic hybridisation may be effected under the conditions disclosed by Sundberg et al [*Plant Science* 43 (1986) 155)] for the production of interspecific hybrids or modifications thereof. An appropriate procedure is as follows.

The protoplast fusion according to the invention is conveniently effected in a protoplast fusion solution (FS-1), containing a buffer such as tris(hydroxymethyl)aminomethanehydrochloride, an osmoticum e.g. a carbohydrate such as mannitol, sorbitol, glucose or sucrose, and potassium and calcium salts. The pH can range from 5.2 to 10, and is preferably about 7.2. The protoplasts of different origin are mixed and concentrated, conveniently to a final density of $10^5$ to $10^6$ protoplasts per ml.

The protoplast mixture should then be left undisturbed for at least 10 minutes to allow the cells to settle at the bottom of the petri dish. The mixture is then treated with polyethyleneglycol (PEG), preferably having a molecular weight from 1500 to 6000. In general good results are obtained when e.g. employing an aqueous solution comprising 40% by weight of PEG (FS-2) at a volume ratio FS-1 to FS-2 of from 10:1 to 1:1. FS-2 comprises conveniently an osmoticum and a calcium salt. The cells are incubated in FS-2 for 1 to 20 minutes depending on the fragility of the cells.

The fusion is accomplished by washing e.g. twice, with fusion solutions containing PEG, in a lower concentration than in FS-2, an osmoticum (e.g. glucose or sorbitol) in a concentration giving a lower osmolarity than FS-2 and a magnesium salt.

Temperatures at which the fusion procedure is suitably carried out range between 20° and 24° C., preferably 22° C.

The concentration of PEG in the "washing solutions" is gradually decreased with each consecutive washing step (see e.g. Example 9 and fusion solutions 3 and 4).

Each washing step should take at least 2 minutes to allow the protoplasts to adjust slowly to the lover osmolartiy of the medium, to avoid bursting of the cells.

After the washing steps have been accomplished the fused protoplasts are placed in an appropriate culture medium. The density of the protoplasts should be in the range of from $10^5$ to $10^6$ protoplasts per ml.

Alternatively such protoplast fusion can be carried out by employing electric current.

For the purpose of electrofusion, chains of protoplasts, consisting of lines of max 8 cells, e.g. 5 cells, are subjected to a direct current (DC)-pulse ranging from e.g. 400 to 1000V/cm with a pulse duration of e.g. 10 to 50 $\mu$s. The thus fused protoplasts are conveniently retained for some time in the electric field e.g. 1 to 2 seconds, before the electric field is turned off to give the protoplasts some time to regain their round shape.

The chains of protoplasts may be prepared in a manner known per se, by subjecting the protoplasts to an alternating current (AC)-electric field. Optimal conditions are determined by varying the alternating field frequency, e.g. around 1 MHz, and the voltage up to 150 V/cm, so that the cells are lined up within a few minutes.

The thus obtained fusion products may be regenerated in the presence of non-fused parental protoplasts, or after optical selection from the culture. Such optical selection may be performed by micro-manipulation of the cells, e.g. according to the procedure disclosed by Patnaik et al, *Plant Science Letters* 24 (1982) 105, for the manual isolation and identification of plant heterokaryons, or by using a cell sorter, e.g. according to the procedure disclosed by Glimelius et al, *Plant Science* 45 (1986) 133, for the selection and enrichment of plant protoplast heterokaryons by cell sorting.

When employing the selection strategy, the parental protoplasts are for example stained with fluorescent dyes, e.g. fluorescein isothiocyanate whereby, where one of the fusion partners is of leaf origin, autofluorescence of the chlorophyll may be used for selection.

The thus obtained fusion products are cultivated in an appropriate culture medium comprising a well-balanced nutrient supply for protoplast growth, containing micro- and macro-elements, vitamins, amino acids and small amounts of carbohydrates, e.g. various sugars such as glucose. Glucose serves as a carbon source as well as an osmoticum. The culture medium comprises plant hormones (auxins and cytokins) which are able to regulate cell division and shoot regeneration. Examples of suitable auxins are naphtyl acetic acid (NAA), 2,4-dichlorophenoxyacetic acid (2,4-D) and indoleacetic acid (IAA). Examples of suitable cytokinins include benzyl aminopurine (BAP) and zeatin (Zea). In general NAA and 2,4-D are used in combination with BAP to initiate cell division. The ratio auxin/cytokinin must then be high, e.g. greater than 1.

After 7 to 10 days the concentration of auxins is conveniently diluted by addition of the same culture medium, but without or substantially less auxins. Typical star-shaped microcalla will in general have developed after 3–4 weeks. Such microcalla will then be transferred to a regeneration medium to initiate shoot formation, preferably after adaptation in an intermediate regeneration medium to differences in composition and physical properties between the culture medium and the regeneration medium.

For shoot formation the ratio auxin/cytokinin in the regeneration medium should conveniently be low, e.g. below 1:10. In general it will be preferred to employ the auxin IAA in combination with the cytokinins Zea and BAP for shoot regeneration.

The regeneration media, BR-1 and BR-2 are relatively poor media compared to the culture medium. They contain less vitamins, the content of carbon source is lover, they comprise solely sucrose and xylose as carbon source, and do not contain amino acids and coconut milk. The regeneration media also have a higher viscosity than the culture medium. BR-1 is semi-solid and contains the growth regulators NAA, 2,4-D and BAP, with the ratio of auxin to cytokinin being less than 1. BR-2 contains Zea and BAP and optionally IAA.

After 4–6 weeks regeneration in BR-1 medium calli of approximately 3 mm in diameter are transferred to BR-2 regeneration medium containing a low sucrose concentration. At this stage shoots will develop within 2–3 weeks.

The obtained shoots are then rooted on a basic medium, MS, without additional hormones.

The nuclear DNA and cell organelle DNA of the thus obtained plantlets may then be identified in a manner known per se, e.g. employing suitable restriction endonucleases and comparing the thus obtained DNA digest pattern of the fusion products with that of the parental lines.

*Brassica oleracea* protoplasts and inactivated or nucleus-free protoplasts of an Ogura CMS *Brassica oleracea* plant, employed herein as starting material may be obtained in a manner known per se from the corresponding plant cells.

Cell wall-free cells, i.e. protoplasts are obtained from green plant material e.g. leaf material, and/or from white plant material e.g. etiolated seedlings, cell suspension cultures, roots or bleached plant material, according to conventional methods, e.g. according to the method disclosed by Glimelius, *Physiologia Plantarum* 61 (1984) 38, for the regeneration of hypocotyl protoplasts.

Where optical selection of the fusion products is intended the starting materials will be conveniently selected from a green plant or where they are from-white plant material they will advantageously be stained to facilitate selection.

The inactivated or nucleus-free protoplasts of an Ogura CMS *Brassica oleracea* plant are obtained in a manner known per se from corresponding Ogura CMS *Brassica oleracea* plant cells or protoplasts, e.g. by irradiation or by standard methods known for the removal of the nucleus from cell material such as centrifugation.

The inactivation of the nucleus by irradiation can be effected with the aid of gamma, UV or X-rays.

Where irradiation is effected with an X-ray source, nucleus inactivation will in general be obtained by applying a dose of e.g. 10 krad/min for 3 to 20 minutes.

The appropriate X-ray dosage may for example be established by determining the minimum level of X-ray irradiation killing 100% of the protoplast population: the percentage of dead cells is estimated by counting the number of formed colonies after 10–20 days in culture. To obtain optimal conditions for the development of cell colonies at low density, it is desirable to use a feeder layer, a pre-conditioned culture medium, or an appropriate cell rescue procedure. Upon determination of the minimum dosage required for the inactivation of cell divisions, the protoplasts are exposed to five increments of X-ray level: the minimum dosage, 10 and 20 krad above and below the minimum dosage. The thus obtained protoplasts are then introduced in the process of the invention.

Satisfactory nucleus inactivation in general may also be achieved by gamma irradiation with $^{60}$Co at a dose of 3-30 krad.

Nucleus elimination may also be carried out by incubation of protoplasts in high osmotic medium to obtain nucleus free subprotoplasts.

An appropriate method for the removal of nuclei by ultracentrifugation suitable for the preparation of the nucleus-free protoplast starting material of the invention is disclosed by Spangenberg in the EUROPEAN JOURNAL OF CELL BIOLOGY 39 (1985) 41-45. Cytochalasine-B is advantageously added to facititate the release of the nuclei from the cells.

Ogura CMS *Brassica oleracea* plants may be obtained by classical breeding techniques from *B oleracea* and CMS *Raphanus sativus* (see introductory part of this application).

It will be appreciated that the Brassica plants of the invention may be employed as starting material for the preparation of other *Brassica oleracea* varieties having the desired mitochondria of the Ogura CMS cytoplasm and chloroplasts of normal fertile *B oleracea* and optionally additional desirable traits by in vitro and/or crossing techniques. Such in vitro and crossing techniques are known in the art by the skilled breeder.

Solutions employed in the experiments:

a) TVL Solution 0.3M sorbitol
0.05M $CaCl_2.2H_2O$ pH=5.6-5.8 b) Enzyme Solution 0.6—1% cellulysin
0.1% macerase
dissoloved in BR-1 but with 2×sucrose concentration, no agarose and 10×concentration 2,4-D
pH=5.4-5.8 c) W5 Solution (1L)

18.4 g $CaCl_2.2H_2O$
9.0 g NaCl
1.0 g glucose
0.8 g KCl
pH=5.6-5.8 d) CPW16s (1L)

16% sucrose
0.0272 g $KH_2PO_4$
0.1010 g $KNO_3$
1.4800 g $CaCl_2.2H_2O$
0.2460 g $MgSO_4.2H_2O$
0.00016 g KI
0.000025 g $CuSO_4.5H_2O$ pH=5.5-5.8 e) Fusion Solution-1 (FS-1)

0.15M sorbitol
0.03M $CaCl_2.2H_2O$
0.075M KCl
0.05M tris(hydroxymethyl)aminomethanehydrochloride
pH=7.2 f) Fusion Solution-2 (FS-2)

30-40% PEG (mw 1500)
0.3M glucose
50 mM $CaCl_2.2H_2O$ g) Fusion Solution-3 (FS-3)

13.3% PEG (mw 1500)
0.1M glucose
0.067M sorbitol
0.067M $CaCl_2.2H_2O$ h) Fusion Solution-4 (FS-4)

6.7% PEG (mw 1500)
0.5M glucose
0.083M sorbitol
0.083M $CaCl_2.2H_2O$

TABLE 1

| COMPOSITION OF THE MEDIA (mg/l) | | | | | |
|---|---|---|---|---|---|
| | MS | BC-1 | BC-2 | BR-1 | BR-2 |
| $KNO_3$ | 1900 | 1900 | 1900 | 2500 | 2500 |
| $NH_4NO_3$ | 1650 | 600 | 600 | 250 | 250 |
| $MgSO_4.2H_2O$ | 370 | 300 | 300 | 250 | 250 |
| $KH_2PO_4$ | 170 | 170 | 170 | — | — |
| $CaCl_2.2H_2O$ | 440 | 600 | 600 | 300 | 300 |
| KCl | — | 300 | 300 | — | — |
| $NaH_2PO_4.H_2O$ | — | — | — | 150 | 150 |
| $(NH_4)_2SO_4$ | — | — | — | 134 | 134 |
| KI | 0.83 | 0.75 | 0.75 | 0.75 | 0.75 |
| $MnSO_4.4H_2O$ | 22.3 | 10 | 10 | 10 | 10 |
| $H_3BO_3$ | 6.2 | 3 | 3 | 3 | 3 |
| $ZnSO_4.2H_2O$ | 8.6 | 2 | 2 | 2 | 2 |
| $NaMoO_4.2H_2O$ | 0.25 | 0.25 | 0.25 | 0.25 | 0.25 |
| $CuSO_4.5H_2O$ | 0.025 | 0.025 | 0.025 | 0.025 | 0.025 |
| $CoCl_2.6H_2O$ | 0.025 | 0.025 | 0.025 | 0.025 | 0.025 |
| Fe-EDTA | 43 | 43 | 43 | 43 | 43 |
| Thiamine-HCl | 0.1 | 10 | 10 | 10 | 10 |
| Pyridoxine-HCl | 0.5 | 1 | 1 | 1 | 1 |
| Nicotinic acid | 0.5 | 1 | 1 | 1 | 1 |
| Ascorbic acid | — | 2 | 2 | — | — |
| Sodiumpyruvat | — | 20 | 20 | — | — |
| Citric acid | — | 40 | 40 | — | — |
| Maleic acid | — | 40 | 40 | — | — |
| Fumaric acid | — | 40 | 40 | — | — |
| Glycine | 2 | — | — | — | — |
| Fructose | — | 250 | 250 | — | — |
| Ribose | — | 250 | 250 | — | — |
| Xylose | — | 250 | 250 | 250 | 250 |
| Mannose | — | 250 | 250 | — | — |
| Rhamnose | — | 250 | 250 | — | — |
| Cellobiose | — | 250 | 250 | — | — |
| Sorbitol | — | 250 | 250 | — | — |
| Mannitol | — | 250 | 250 | — | — |
| Inositol | 100 | 100 | 100 | 100 | 100 |
| Sucrose | ** | 250 | 250 | 70000 | 5000 |
| Glucose | — | 68400 | 68400 | — | — |
| Casamino acid | — | 250 | 250 | — | — |
| Coconut water* | — | 20 | 20 | — | — |
| Agarose | — | — | — | 2000 | 4000 |
| Agar | 6000 | — | — | — | — |
| NAA | — | 0.1 | 0.1 | 0.1 | — |
| 2,4-D | — | 1 | — | 0.1 | — |
| IAA | — | — | — | — | (0.1) |
| Zeatin | — | — | — | — | 1 |
| BAP | — | 0.5 | 0.5 | 0.5 | 0.5 |

*ml/l
**see examples

EXAMPLES

Example 1

Seed Sterilisation and Germination

Seeds of *Brassica oleracea*, Delira type cauliflower with CMS cytoplasm from *Raphanus sativus* CMS Ogura (hereinafter designated *B oleracea* A 61043) are briefly dipped in 20% alcohol and sterilised in a 1% sodium hypochlorite solution for 20 minutes on a gyrotary shaker at 160 rpm at 22° C. Afterwards extensive rinsing with sterile distilled water is required. The seeds are placed on the MS nutrient medium (see Table 1), with 1% sucrose and without hormones. To obtain green sterile plantlets, the seeds are grown on replica plates in the light (3000 lux), 16 hr photoperiod at 22° C. Sterile shoots are subcultured under the same conditions in plastic containers.

To obtain white tissue for protoplast isolation, e.g. hypocotyls, the seeds are grown in petri plates in the dark at 22° C.

Example 2

Analagous to the procedure of Example 1, seeds of *Brassica oleracea*, cultivar SG 121[(a)], (cauliflover) are sterilised and germinated.

(a) deposited Dec. 8, 1987 at the American Type Culture Collection under ATCC designation number 40399.

Example 3

Isolation of Protoplasts

Four week old sterile shoots of plant material according to Example 1 are cut into small pieces and preplasmolysed for approximately 1 hour in TVL solution in the dark.

TVL solution is removed and a check for bacterial contamination of the plant material is done, by means of culturing a part of the incubated TVL solution over night in bacterial medium at 22° C.

To the material is added an enzyme solution, containing 0.6-1% cellulysin and 0.1% macerase and the material incubated for 16 hours in the dark at 22° C.

The suspension is then filtered through nylon mesh (70μm) and washed with half volume of CPW16s solution by centrifugation at 750 rpm for 7 minutes. This results in floatation of the intact protoplasts. The protoplasts are collected and rinsed first with W5 solution and then washed with fusion solution-1 by centrifugation at 500 rpm for 5 minutes.

Example 4

Eight day old hypocotyls of the plant material according to Example 1 are isolated according to the process of Example 3, except that during the enzyme treatment lug/ml of fluorescein isothiocyanate is added. In this way stained protoplasts suitable for hand or machine selection are obtained.

Example 5

Seeds of *Brassica oleracea*, cultivar SG 121 (cauliflower) are sterilised and germinated according to the procedure of Example 1, and 4 week old sterile shoots thereof are then treated according to the procedure of Example 3, to give protoplasts of *B oleracea*, cultivar SG 121.

Example 6

Seeds of *B oleracea*, cultivar SG 121 (cauliflower) are sterilised and germinated according to the procedure of Example 1, and 8 day old hypocotyls thereof are then treated according to the procedure of Example 3, except that during the enzyme treatment 1 μg/ml of fluorescein isothiocyanate is added to give stained protoplasts suitable for hand or machine selection.

Example 7

Irradiation of Protoplasts

Freshly isolated protoplasts according to Example 3 are plated in a 6 cm petri dish in W5 solution (2 ml). The protoplasts are irradiated using an X-ray source (Baltobloc CE 100), at a dose of 10 krad/min, for 5 to 20 minutes. After irradiation, the inactivated protoplasts are diluted in fusion solution-1 before being used for fusion experiments.

Example 8

Cytoplast Isolation by Ultracentrifugaton

A gradient consisting of 10 ml water saturated with sucrose and a top layer of 4 ml 1.5M sorbitol, containing 0.5% dimethyl sulfoxide (DMSO) and 30 μg/ml cytochalasine-B and 2ml ($=1\times10^6$) protoplasts according to Example 3 in fusion solution-1 are loaded on top thereof. The material is subjected to centrifugation for 15 minutes at $40,000\times g$ at 25° C., to give nucleus-free cytoplasts of *B oleracea* A 61043.

Example 9

Fusion Procedure

Protoplasts according to Examples 5 and 7 are mixed 1:1 in a final concentration of $5\times10^5$ protoplasts (pps)/ml fusion solution-1 in a sterile chamber under sterile air flow.

Droplets of 200 μl are placed in an uncoated petri dish (5–7 droplets per 6 cm petri dish), and are allowed to settle for 15 minutes. (The sterile air flow is turned off to avoid disturbance of the settling protoplasts.) Fusion solution-2 (25–100 μl per droplet) is added to induce agglutination for 3–7 minutes.

The sterile air flow is turned on again, and the solution is replaced by fusion solution-3 for 5 minutes. Then the solution is replaced by fusion solution-4 for 5 minutes. Finally the fusion solutions are replaced with 1.5 ml culture medium (BC-1).

Example 10

Selection and Growth of Fusion Products

Fused cells, which can be recognised visually by the presence of double fluorescence are picked up with a micromanipulator.

Hybrids or cybrids are cultured in Biopor filter membranes, diameter 1.1 cm or 3 cm with pore width of 0.45-3 μm, containing 100 to $10^5$ cells per ml of culture medium-1. The filters are placed in a petri dish containing 2-2.5 ml feedercells ($10^5$ per ml) and the material is incubated at 22° C. in the dark.

When 20% of the cells are dividing, culture medium-2 is added.

When typical star-shaped microcalla have developed, they are transferred to regeneration medium-1 (BR-1) in coated petri dishes and cultured at 22° C. and 500 lux for 4–6 weeks.

Example 11

Stained hypocotyl protoplasts according to the procedure of Example 4 are irradiated according to the procedure of Example 7. Thus obtained inactivated, stained protoplasts are fused with the protoplasts according to Example 5 and the fused protoplasts then selected employing a cell sorter equipped with a mercury lamp (HB 100) for two parameter fluorescence sorting.

The fluorescence excitation beam of the cell sorter is set between 488 nm and 500 nm. The emission beam coming from the excited cells is split by "dichroic" mirrors into two light beams: one with wavelengths between 560 and 610 nm, representing the autofluorescence of the chloroplasts, and the other with wavelengths between 500 and 560 nm, representing the fluorescein isothiocyanate fluorescence. Two photomultipliers are used to measure these signals. The sheath fluid (carrier fluid used in the cell sorter to dilute the protoplast sample into a continuous liquid stream) contains autoclaved and degassed V5 medium.

The sorting is based on the principle that fluorescence of non-fused parental cells show only single fluorescence (red fluorescence of leaf mesophyll protoplasts or fluoresceins isothiocyanate yellow/green fluorescence of the stained hypocotyl protoplasts) while fused cells will show double fluorescence (red and yellow/green).

Sorted hybrids or cybrids are cultured in a manner identical to that used for cells selected by micromanipulation.

Example 12

The entire fusion mixture according to Example 9 is kept in the petri dish in which the fusion was performed and cultured in the dark at 22° C. After 1–2 days the cells are pipetted and transferred to a coated petri dish. After about 7–14 days when 10% of the cells are dividing, two volumes of culture medium-2 (BC-2) are added. After 10 days another volume of BC-2 is added. The cells are still cultured in the dark at 22° C. After 2–4 weeks, when the cells have formed typical, star-shaped microcalli, they are transferred to regeneration medium-1. The microcalli are cultured in low light intensity (500 lux), 16 hour photoperiod at 22° C.

Example 13

Plant Regeneration

The calli according to Example 10 and Example 12, having developed to a size of 2–5 mm in diameter are transferred to regeneration medium-2-(BR-2) and cultured at 22° C. and 3000 lux, 16 hour photoperiod. Shoots of about 1 cm are transferred to MS medium with 1% sucrose without hormones and rooted on the same MS medium.

Example 14

Molecular Analysis of the Fusion Products a) Nuclear DNA Composition

Characterisation of the nuclear composition of the fusion products is effected by using specific DNA probes. A 0.9 kb Kpn I/Bam HI fragment of the beta-tubulin gene of *Arabidopsis thaliana* hybridises with various bands in an endonuclease digest pattern of nuclear DNA of the CMS donor, *B oleracea* A 61043. This pattern is specific for *B oleracea* A 61043 and differs from the *B oleracea* breeding lines that are used as acceptor for the CMS trait (FIG. 1 Panel A).

b) Mitochondrial DNA Composition

Characterisation is effected with pBO 604 DNA, a clone containing a 1.5 kbp Sac I fragment from the mitochondrial DNA of Ogura CMS cytoplasm of *Raphanus sativus*. This clone gives hybridisation signals with restriction endonuclease digests of mitochondrial DNA from Ogura CMS cytoplasms of *B oleracea*, A 61043 but not with mitochondrial DNA from fertile cytoplasm of *B oleracea* breeding lines (FIG. 1 Panel B), c) Chloroplast DNA Composition The DNA present in the chlorosis sensitive chloroplasts of the Ogura CMS cytoplasm is characterised with the probe lambda Bcp 17. This clone contains a 4.5 kop I/Sac I fragment from Ogura CMS chloroplast DNA. The clone hybridises with a 57.5 kpb band in the Sal I digest of Ogura CMS chloroplast DNA and with a 9.9 kbp band in the Sal I digest of chloroplast DNA from fertile cytoplasms in *B oleracea* breeding lines (FIG. 1 Panel C).

The FIG. 1 panel A, panel B and panel C are accurate hand drawn copies of photographs.

What is claimed is:

1. CMS *Brassica oleracea* plants containing mitochondria of the Ogura CMS cytoplasm, chloroplasts of fertile *Brassica oleracea*, and nuclear material of a fertile *Brassica oleracea*.

2. Plants according to claim 1 which are selected from the group consisting of cauliflower, white cabbage, Brussels sprouts, and broccoli.

3. Diploid CMS *Brassica oleracea* plants containing mitochondria of the Ogura CMS cytoplasm and chloroplasts of fertile *Brassica oleracea*.

4. Plants according to claim 3 which are selected from the group consisting of cauliflower, white cabbage, Brussels sprouts, and broccoli.

5. A process of making *Brassica oleracea* plants of claim 1 comprising:
   a) fusing protoplasts of *B. oleracea* with protoplasts of an Ogura having inactivated nuclei CMS *B. oleracea*;
   b) regenerating the thus obtained allogenic cells or their progeny into CMS *B. oleracea* plants; and
   c) optionally employing the CMS *B. oleracea* plants of b) for further propagation or crossing.

6. A process of making *Brassica oleracea* plants of claim 2 comprising:
   a) fusing protoplasts of *B. oleracea* with protoplasts of an Ogura CMS *B. oleracea* having inactivated nuclei;
   b) regenereation the thus obtained allogenic cells or their progeny into CMS *B. oleracea* plants; and
   c) optionally employing the CMS *B. oleracea* plants of b) for further propagation or crossing.

* * * * *